United States Patent
Wang et al.

(10) Patent No.: US 6,522,402 B1
(45) Date of Patent: Feb. 18, 2003

(54) APPARATUS AND METHOD FOR ANALYZING MICROSCOPIC SAMPLES BASED ON OPTICAL PARAMETRIC OSCILLATION

(75) Inventors: Zifu Wang, Irvine, CA (US); George R. Rossman, Pasadena, CA (US); Geoffrey A. Blake, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 09/302,753

(22) Filed: Apr. 30, 1999

Related U.S. Application Data
(60) Provisional application No. 60/083,730, filed on Apr. 30, 1998.

(51) Int. Cl.[7] .................................................. G01J 3/28
(52) U.S. Cl. ........................................ 356/327; 356/326
(58) Field of Search ................................. 356/326, 327, 356/434, 435

(56) References Cited

U.S. PATENT DOCUMENTS

| | | | |
|---|---|---|---|
| 4,740,082 A | * 4/1988 | Young | 356/346 |
| 5,317,156 A | * 5/1994 | Cooper et al. | 250/345 |
| 5,329,353 A | * 7/1994 | Ichimura et al. | 356/301 |
| 5,657,119 A | * 8/1997 | Kawasaki et al. | 356/326 |
| 5,812,305 A |   9/1998 | Blake et al. | 359/350 |
| 5,930,000 A | * 7/1999 | Brand | 356/437 |
| 6,040,914 A | * 3/2000 | Bortz et al. | 250/345 |

OTHER PUBLICATIONS

J. G. Haub, M. J. Johnson, and B. J. Orr; Spectroscopic and nonlinear–optical applications of a tunable β–barium borate optical parametric oscillator; Sep. 1993; Optical Society of America, vol. 10, No. 9.

* cited by examiner

*Primary Examiner*—Zandra Smith
(74) *Attorney, Agent, or Firm*—Fish & Richardson P.C.

(57) ABSTRACT

A tunable spectrometer configured to microsample minute samples of dimension on the order of 10 μm or less. A tunable optical parametric oscillator laser is used to produce a sampling beam and a reference beam for measuring the absorption of the samples.

11 Claims, 4 Drawing Sheets

APPARATUS AND METHOD FOR ANALYZING MICROSCOPIC SAMPLES BASED ON OPTICAL PARAMETRIC OSCILLATION This application claims the benefit of U.S. Provisional Application No. 60/083,730, filed on Apr. 30, 1998.

ORIGIN OF THE INVENTION

The U.S. government may have certain rights in the invention which was made under U.S. Government Contract No. EAR 92-18980, awarded by the National Science Foundation.

TECHNICAL FIELD

This specification generally relates to apparatus and methods for analyzing properties of materials, and more specifically, for performing spectroscopic measurements.

BACKGROUND

Detection and analysis of microscopic particles by spectroscopic determination of their chemical constituents or composition can be used in various applications, such as detection of a minute amount of a substance, especially in small areas less than 10 µm. Such techniques may be used in, for example, detecting narcotic or explosive particles on a surface, presence of biological substances in a sample, examining the process uniformity of diffusion during fabrication of semiconductor substrates or crystal wafers, or measuring properties of samples under extreme conditions such as high temperature, high pressure, or both.

One widely-used spectroscopic technique uses a Fourier-transform infrared (FTIR) spectrometer which is based on a Michelson interferometer. A beam from a light source is split into two beams. One is reflected by a fixed mirror and another one is reflected by a movable mirror. The two reflected beams are recombined by the beam splitter as a single beam whose intensity is modulated due to interference. The interference pattern is a function of the relative spatial displacement of the movable mirror relative to the fixed mirror and is associated with the Fourier transform of the spectrum of the recombined beam.

When this recombined beam transmits through or reflects from a sample, it carries the spectral information of the sample through optical interaction with the sample by spectral components therein. Hence, spectral information about the sample can be extracted by performing a Fourier transform of the intensity variation of the received recombined beam.

One of important components of the FTIR spectrometer is the light source. The radiation spectral range of the light source ultimately determines the spectral range of the spectrometer. A wide-band light source, such as a heated ceramic material, is often used. This wide spectral range of the light source allows parallel and simultaneous processing of spectral information at all wavelengths by the FTIR spectrometer. As a result, FTIR spectrometers can provide high-speed spectral analysis and have been used in various on-line process monitoring applications. However, certain disadvantages are also associated with such a wide-band light source.

For example, the light intensity from a wide-band light source at each wavelength within the spectral band is quite low. This limits the detection sensitivity in measuring minute quantities of substances in a sample since the signal at a particular wavelength of interest can be so weak as to produce an unacceptably low signal-to-noise ratio. Use of a long integration time can be impractical in many applications.

In addition, the spatial resolution of the spectroscopic analysis in such FTIR spectrometers is also limited when analysis of microscopic samples with small dimensions (e.g., less than 10 µm) is desired. This type of microsampling application presents a number of technical obstacles to conventional FTIR spectrometers. For example, since the spatial extent of samples is small, only a limited amount of light of all wavelengths within the spectral band can be directed through or onto the samples. Also, the light intensity at each wavelength is further limited since it is only a small fraction of the limited total amount of light.

One way to obviate the above and other limitations associated with the conventional FTIR spectrometers is to replace the conventional wide-band light sources with the synchrotron radiation emitted by accelerated charged particles. See, for example, Lu et al, Trans. Amer. Geophys. Union. 77(46), F661 (1996). However, a synchrotron source is essentially a circular particle accelerator and is prohibitively expensive and physically large. Although an FTIR spectrometer based on a synchrotron source may have limited use in large-scale scientific research, use of a synchrotron source is impractical for most scientific and industrial applications.

A further limitation of a FTIR spectrometer is the optical condensing and collecting units associated with the use of a wide-band light source. Special care is required to design such optical units in order to reduce various optical aberrations, including chromatic aberration. Schmidt-Cassegrain systems, which have two concentric spherical reflectors, are often used for both focusing the wide-band light onto the sample and collecting the light from the sample. This can significantly complicate the design and maintenance of the optical system in FTIR microsampling spectrometers.

SUMMARY

In recognition of the above, the present disclosure provides apparatus and method based on a different approach to detection and analysis of microscopic samples in minute quantities. The apparatus includes a special combination of a tunable optical parametric oscillator (OPO) laser and an absorption optical system to form a tunable absorption spectrometer.

One embodiment of the apparatus includes a beam splitter to divide a monochromatic beam from the OPO laser into a reference beam and a sampling beam, a reference photodetector to convert said reference beam into a reference electrical signal indicating an intensity of the sampling beam, a sampling aperture with a dimension less than 10 µm positioned to limit a spatial extent of the sampling beam, a sample holder adapted to hold a sample relative to the sampling aperture to expose the sample to the sampling beam, and a sampling photodetector to convert transmitted light from the sample into a sampling electrical signal. A control circuit is also provided to control the wavelength of the OPO laser and to process said reference and sampling electrical signals to produce absorption data as a function of the wavelength of the sampling beam.

One embodiment of the microsampling method includes the following steps:

generating a tunable monochromatic laser beam from optical parametric oscillation;

reducing the dimension of the laser beam to increase an intensity above a specified level;

dividing the laser beam into a reference beam and a sampling beam;

measuring and using the intensity of the reference beam to indicate an intensity of the sampling beam;

using a sampling aperture with a dimension less than 10 μm to limit spatial extent of the sampling beam;

exposing a sample to the sampling beam that transmits through the sampling aperture;

measuring the intensity of transmitted light from the sample; and tuning the wavelength of the laser beam to obtain the absorption spectrum of the sample.

These and other aspects and associated advantages will become more apparent in light of the following detailed description, the accompanying drawings, and the appended claims.

DETAILED DESCRIPTION

Spectroscopic information about a substance can be obtained by illuminating the substance with light at one or more resonant wavelengths associated with that substance and by measuring the transmitted, reflected, or scattered light from the substance. A relatively high intensity of such light is often desirable in order to achieve an acceptable signal-to-noise ratio for a quantitative analysis, especially when small quantities of the substance in small volumes are being detected. A physically small substance may have a dimension equal to or less than 10 μm. Hence, the intensity of the light at each resonant wavelength of the substance may be required to be above a minimum level. Examples of such applications include microsampling a small amount of a sample, a small area of a large sample, or a sample confined in a small vessel or chamber.

The apparatus and method of the present disclosure use a tunable OPO laser to produce a large number of photons at each resonant wavelength of the substance, to extract spectral information of the substance at that wavelength. Then the OPO laser is then tuned to another wavelength to perform additional measurements. This process repeats at all desired wavelengths within a spectral band of interest.

Hence, rather than distributing the available photon energy among multiple wavelengths within a broad spectral band as in Fourier transform spectrometers, the approach here is to concentrate the available photon energy from the OPO laser at a single wavelength at a time to achieve a desired signal-to-noise ratio from a microscopic sample.

An optical absorption system is used in the apparatus to measure the absorption of the sample one wavelength at a time. The intensities of an incident beam to the sample and the transmitted beam from the sample are measured and calibrated to produce absorption measurements of the sample. This special combination of the tunable OPO laser and the optical absorption system provides a tunable and highly sensitive absorption spectrometer that is capable of microsampling. This microsampling can be on the scale of about 10 μm or less which is beyond the capabilities of many FTIR spectrometers and prior absorption spectrometers.

Figure 1:
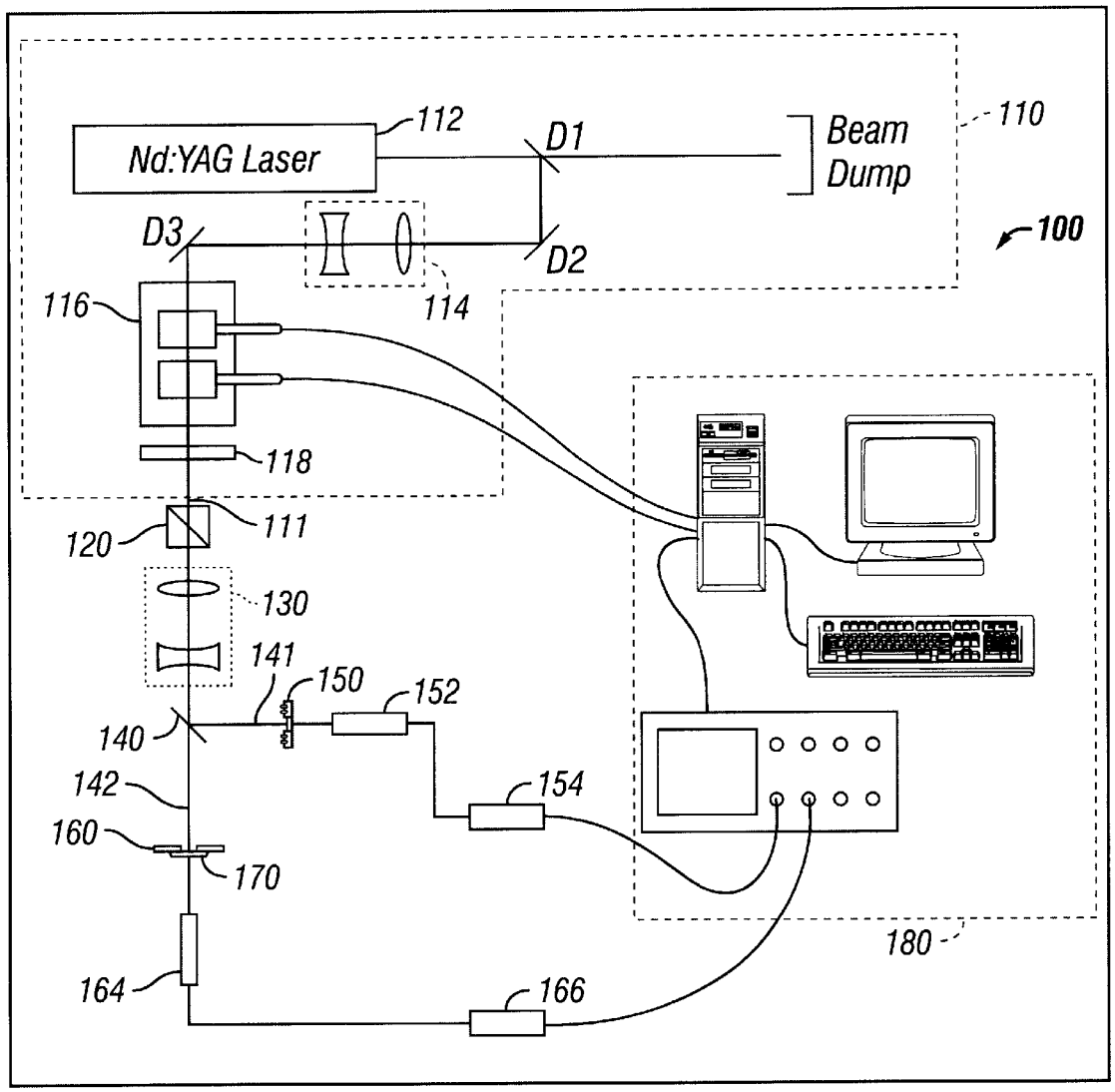
FIG. 1 shows one embodiment of a tunable optical parametric oscillator (OPO) absorption spectrometer.

FIG. 1 shows one particular embodiment of the tunable OPO absorption spectrometer 100. A tunable OPO laser 110 includes a pump source 112 (e.g., a pulsed solid-state laser), an optical telescope 114 which reduces the cross section of the pump beam, an OPO cavity 116 with two nonlinear optical crystals suitable for optical parametric oscillations, and a wavelength filter 118 to select the wavelength of the OPO laser. A second telescope 130 is placed to reduce the cross section of the OPO laser beam 111 and hence increase the beam intensity. A beam splitter 140 splits the OPO laser beam 111 into two beams including a reference beam 141 and a sampling beam 142.

The reference beam 141 provides a measurement of the power or intensity of the sampling beam 142 for calibration of the absorption measurements. A reference pinhole 150, and a photodetector 152 are used to receive and measure the power of the reference beam 141. The reference pinhole 150 (e.g., 25 μm in diameter) is used to reduce the amount of light received by the detector 152 so that the output signal is comparable in magnitude to the signal measured after the sample. An amplifier 154 may be coupled to the photodetector 152 to amplify the signal if so desired.

A sampling pinhole 160 is positioned in the optical path after the beam splitter 140 to confine the spatial extent of the sampling beam 142. The aperture of sampling pinhole 160 determines the spatial resolution of the microsampling of the OPO spectrometer 100. The aperture dimension of the sampling pinhole 160 may be around 15 μm or less. Sampling pinholes from 5 μm to 12.5 μm have been used to demonstrate the microsampling capabilities. The aperture of the sampling pinhole 160 is preferably approximately 10 μm or less, or more preferably about 5 μm or less, while the OPO laser 110 and other components are properly adjusted to produce a sufficiently large signal-to-noise ratio (e.g., at least greater than 10) for quantitative analysis.

A sample holder 170 is used to hold a sample under measurement against or in close proximity to the sampling pinhole 160. The sample holder 170 may include a translational stage to shift the position of the sample relative to the sampling pinhole 160 so different parts of the sample can be exposed to the confined sampling beam 142 for measurements. A sampling photodetector 162 measures the power of the sampling beam transmitted from the sample. The signal from the sampling photodetector 162 may be amplified if needed by an amplifier 164.

A control unit 180 is implemented to control the operation of the OPO laser 110 and the sampling measurements and to provide a user interface. The control unit 180 can tune the OPO cavity 116 to adjust the wavelength of the OPO laser beam 111. The output signals from the photodetectors 152 and 162 are sent to the control unit 180 for data processing and analysis. A microprocessor and a display device may be included in the control unit 180. The position of the sample holder 170 may also be controlled by the control unit 180.

One aspect of the spectrometer 100 of FIG. 1 is its capability of projecting a high-intensity sampling beam 142 of a well-defined polarization at the sample holder 170. The polarization property of the sampling beam 142 can provide important information on a sample. For example, measurements of certain crystal samples may require the polarization of the sampling beam 142 to be at a specific angle relative to a selected direction of the crystal samples. The OPO laser beam 111 in general has a linear polarization that is defined by the OPO cavity 116. A linear polarizer 120 can be placed in the optical path of the beam 111, with its polarization axis substantially aligned with the polarization of the beam 1111, to maintain the polarization of the sampling beam 142. Hence, any fluctuation in the polarization of the beam 111 (e.g., due to perturbations to the OPO cavity 116) can be thus eliminated in the sampling beam 142. The orientation of the sample on the sampler holder 170 can be adjusted with respect to the polarization of the polarizer 120.

The telescope 130 is used here not only to reduce the cross sectional area of the beam 111 to increase its intensity but also to preserve the polarization at the direction defined by the polarizer 120 and maintain the uniformity of the polarization of the beam. Contrary to a focusing action of a lens system used in many spectrometers where a sampling beam is directly focused onto a sample to achieve a desired high intensity, the spectrometer 100 of FIG. 1 uses the telescope 130 to project a substantially collimated sampling beam 142 to the sample. The telescope 130 reduces the diameter of the beam 111 without making it convergent. Hence, the degradation of the purity of the beam polarization caused by bending the rays of a beam in focusing can be avoided. As a result, polarization-sensitive quantitative measurement can be performed with the spectrometer 100 with high precision.

Figure 2:
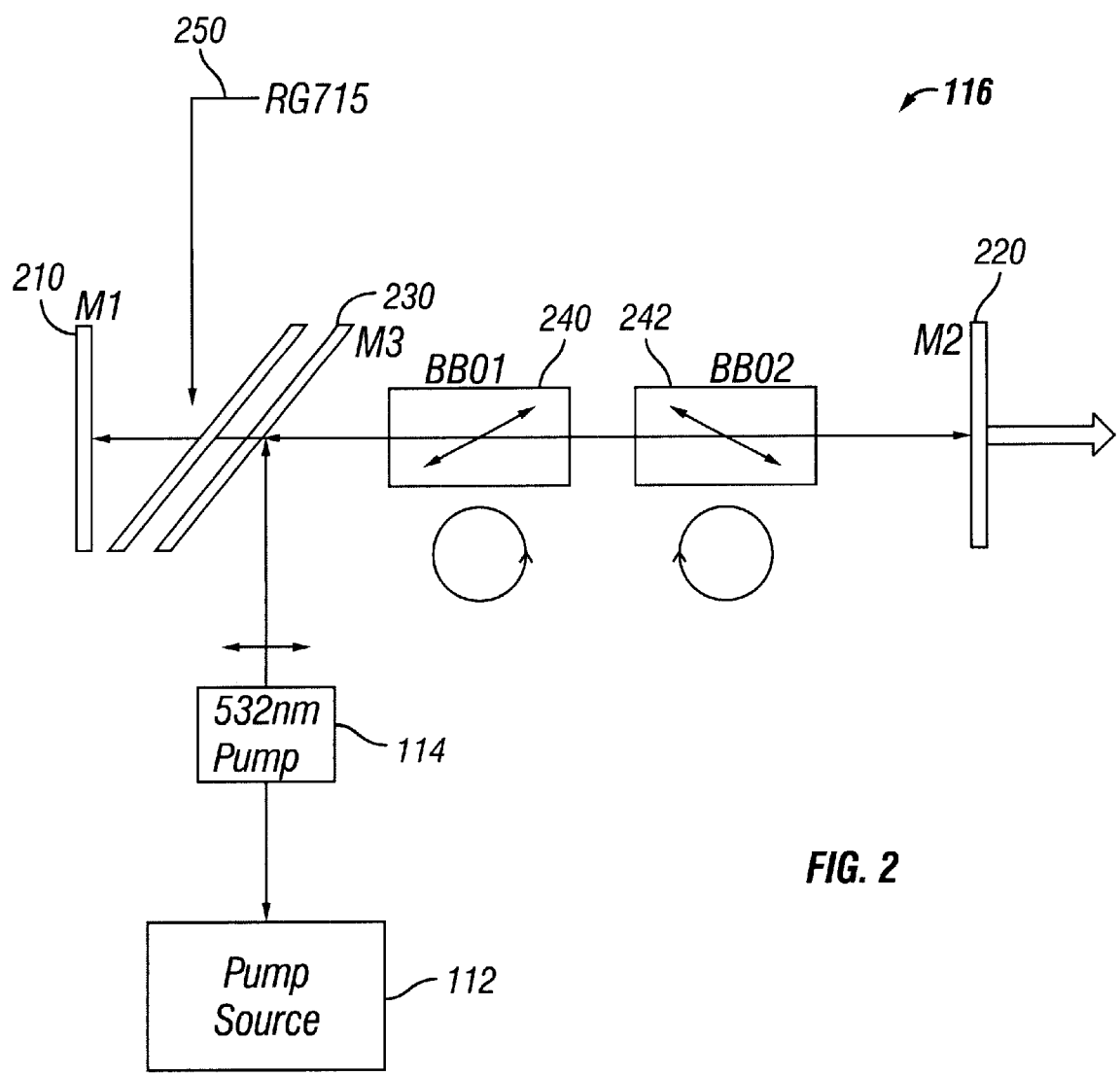
FIG. 2 shows one example of an OPO laser.

The OPO laser 110 may have a number of configurations. U.S. Pat. No. 5,812,305 to Blake et al. discloses some tunable OPO configurations suitable for the spectrometer 100 in FIG. 1. FIG. 2 shows another optical arrangement for the OPO laser 110. The pump source 112 may be a Q-switched solid-state pulsed laser. For example, a neodymium-doped yttrium aluminum garnet (Nd:YAG) laser can be used. Such a YAG laser may produce pulses at 532 nm (second harmonic generation) with a width of about 7 ns at a repetition rate of 30 Hz or higher. Each pulse may be about 80 mJ with a far-field beam diameter of about 7.5 mm. The telescope 114 reduces the YAG beam to about 3.5 mm in order to lower the OPO threshold.

The OPO cavity 116 includes a plano rear mirror 210 and a plano output coupling mirror 220. The rear mirror 210 may be coated with a Ag reflecting film. The front output coupling mirror 220 is a normal incidence dichroic reflector on a sapphire substrate optimized to be reflective at the pump wavelength and substantially transmissive at the signal and idler wavelengths. The reflectivity of the mirror 220 is about 4% to 5% at the signal and idler wavelengths. This can be achieved without dielectric coating on a transparent plano substrate. A pump input coupler 230 is placed between the mirrors 210 and 220 to couple the pump beam into the OPO cavity 116 with its polarization in the P-polarization. A 45° dichroic reflector for P-polarized pump light may be used and the reflectivities for the S-polarized light and the P-polarized light are about 1.6% and 18%, respectively.

Two nonlinear crystals 240 and 242, e.g., two $\beta$-BaB$_2$O$_4$ (BBO) crystals, are mounted on step motors and counter rotate with each other to achieve high conversion efficiency and to compensate beam walk-off within the crystals. The spacing between the mirrors 210 and 220 may be about 7 cm and the two BBO crystals may be 6 mm×12 mm×12 mm. The crystals are cut for the type II phase matching at $\theta=37°$ and $\phi=30°$. The nonlinear operation of the optical parameter process converts one pump photon at $\lambda_p$ into a signal photon at $\lambda_s$ and an idler photon at $\lambda_i$ ($>\lambda_s$). In type II phase matching, the polarization of the signal beam is perpendicular to that of the idler beam. In this case, the signal beam is S polarized while the idler beam is P-polarized.

Both signal and idler beams can oscillate within the OPO cavity 116. A optical filter 250 can be inserted in the OPO cavity 116 to select one of the signal and idler beams to oscillate. A long-pass filter may absorb over 99% of the signal beam and create singly-resonant OPO on the idler beam. The wavelength of the oscillating beam (also the signal beam) is tuned by changing the angles of the two crystals 240 and 242 symmetrically relative to the pump beam. When pumped at 532 nm, the idler beam can be tuned within red and infrared range from about 640 nm to about 3200 nm. The output pulse energy of the idler beam of about 10 mJ can be so generated.

The above OPO laser may also be configured to produce a tunable laser output at a different spectral range. For example, the YAG laser 112 may be configured to produce a third-harmonic generation pump beam at 355 nm. With proper modifications in the OPO cavity 116, the OPO laser can produce a tunable output from about 410 nm to about 710 nm.

Figure 3:
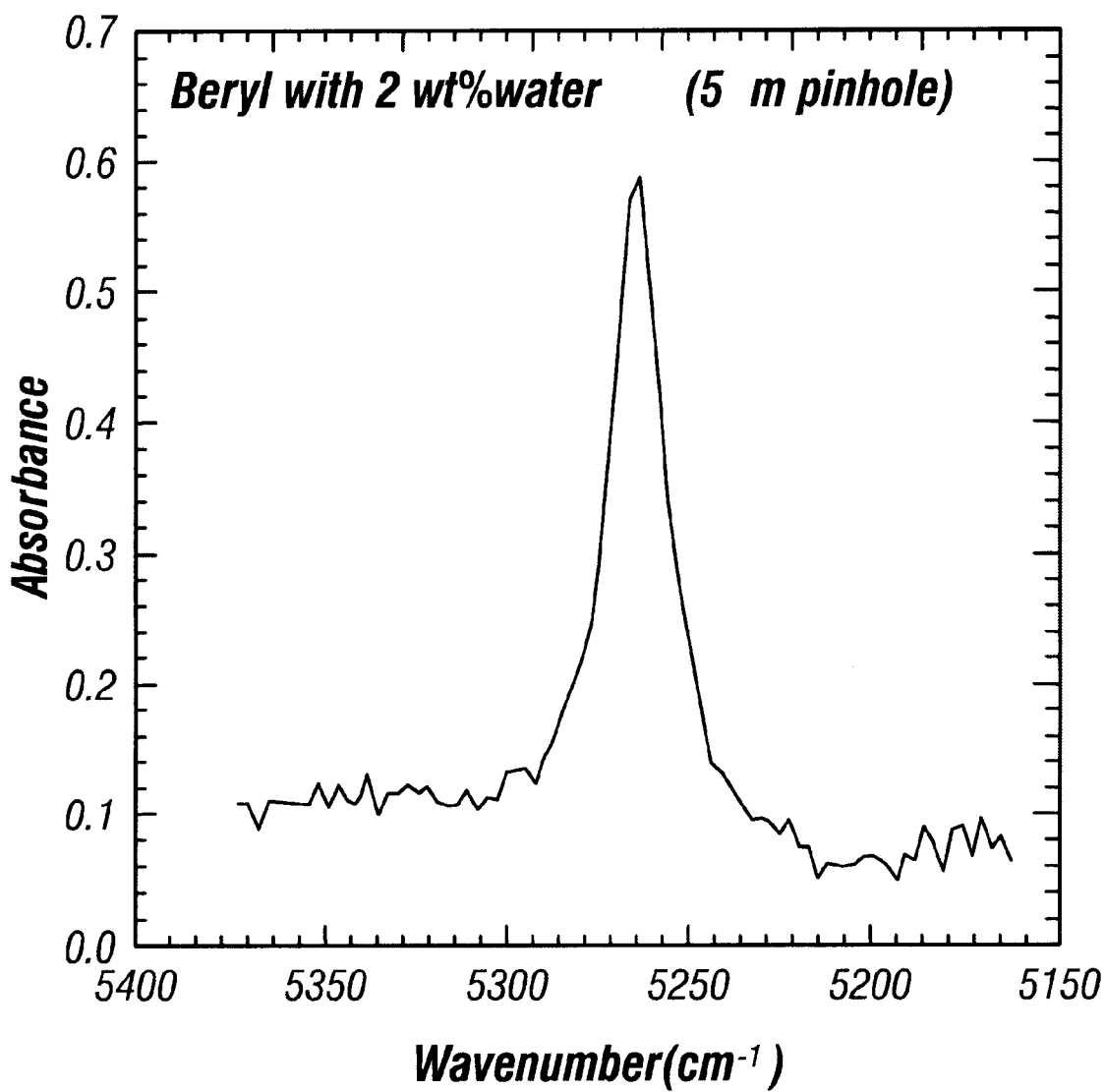
FIGS. 3 and 4 show measured microsampling absorption spectra of beryl containing 2 wt % water and a topaz sample, $Al_2SiO_4(F, OH)_2$, respectively, both of which are acquired with the OPO spectrometer of FIG. 1.
Figure 4:
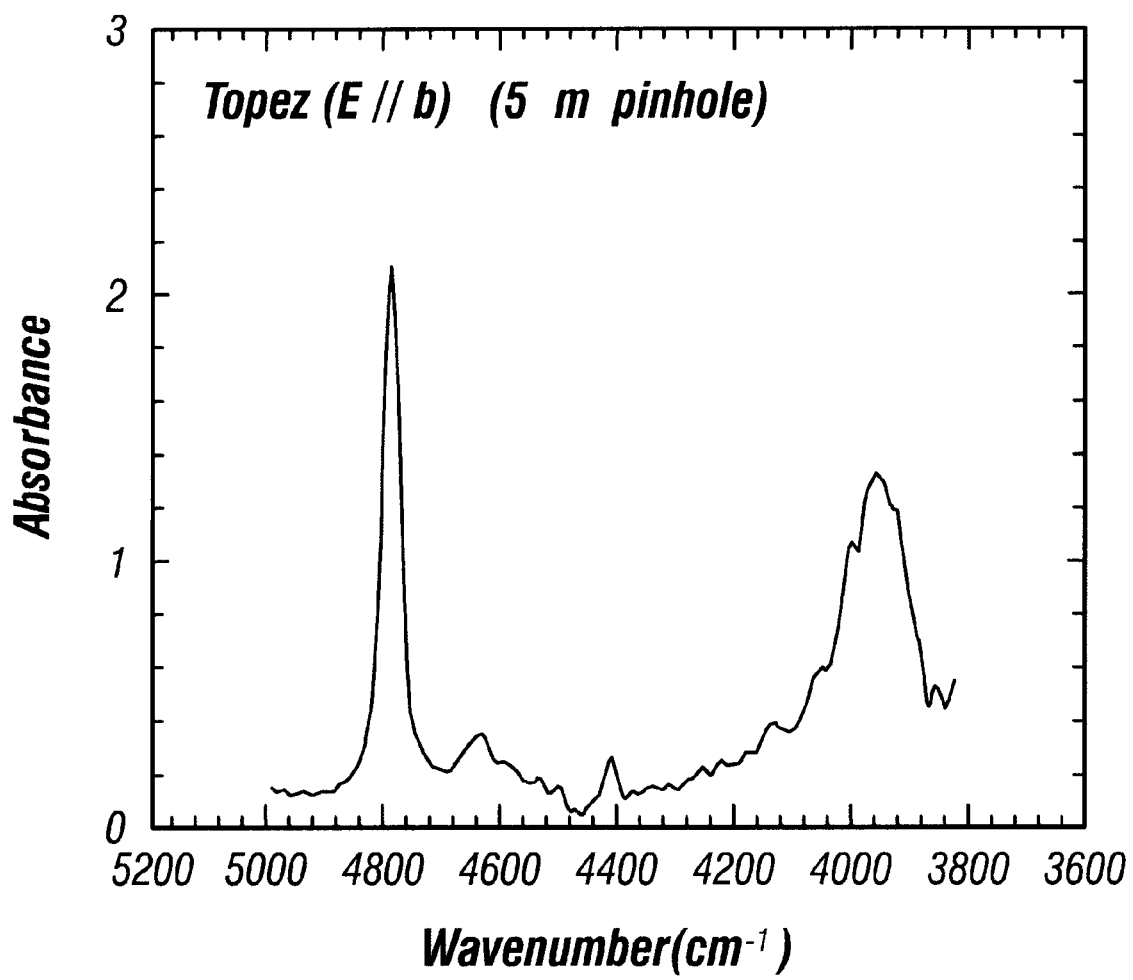

Referring back to FIG. 1, the tunable OPO spectrometer 100 has a relatively simple optical layout and yet can achieve high detection sensitivity and spatial resolution. FIGS. 3 and 4 show measured absorption spectra of beryl containing 2 wt % water and a topaz sample, Al$_2$SiO$_4$(F, OH)$_2$, respectively. Both samples are natural crystals oriented along a crystallographic axis and were prepared in form of a doubly polished plate of about 1 mm in thickness. The sampling pinhole 160 was set at 5 $\mu$m in both measurements. The diameter of the sampling beam 142 was about 1.75 mm. The signal-to-noise ratio of the measurements is about 20, which is sufficient for a precision quantitative analysis. The ratio of the cross sectional area of the sampling beam 142 and that of the sampling pinhole 160 was approximately $1.23 \times 10^{23}$. Hence, the results of FIGS. 3 and 4 demonstrate that the OPO spectrometer can achieve a high detection sensitivity even when more than 99.99% of the sampling beam 142 is blocked.

A special sample chamber may be implemented on the sample holder 170 to produce extreme environments at the sample for certain applications. For example, the chamber may be used to heat a sample at an elevated temperature. The high intensity of the sampling beam 142 from the OPO laser 110 can produce a transmitted signal with a magnitude much higher than the blackbody radiation level of the heated sample and hence allows spectroscopic measurements with high precision, which is beyond capabilities of many conventional spectrometers. The sample chamber may also include a hi-pressure diamond cell which produces high pressures on small samples.

Although a specific embodiment has been disclosed as an example, various modifications and enhancements may be made. For example, the sampling pinhole 160 of FIG. 1 provides a simple microsampling device to use the sampling beam 142 to sample a micro sample less than 10 $\mu$m in size, with a high spatial resolution. Such a microsampling device may be implemented by other more complex techniques such as two-dimensional mastering technique involving programmable arrays (e.g., LCD displays). The OPO laser 110 may be replaced by other OPO lasers with different designs and other tunable lasers with similar output power levels. The linear polarizer 120 may also be placed in the optical path of the sampling beam 142 between the beam splitter 140 and the sample holder 170.

These and other modifications are intended to be encompassed in the following claims.

What is claimed is:
1. A tunable absorption spectrometer, comprising:
   a tunable optical parametric oscillator laser operating to produce a monochromatic beam whose wavelength is tunable in a specified spectral range;

a beam splitter positioned in an optical path of said monochromatic beam to divide said monochromatic beam into a reference beam and a sampling beam;

a reference photodetector to receive and convert said reference beam into a reference electrical signal indicating an intensity of said sampling beam;

a sampling aperture with a dimension less than 10 $\mu$m positioned to limit a spatial extent of said sampling beam;

a sample holder adapted to hold a sample relative to said sampling aperture to expose the sample to said sampling beam that transmits through said sampling aperture;

a sampling photodetector to receive and convert transmitted light from the sample into a sampling electrical signal; and a control circuit coupled to control the wavelength of said laser and to receive said reference and sampling electrical signals, said control circuit configured to produce absorption data as a function of the wavelength of said monochromatic beam.

2. A spectrometer as in claim 1, wherein said laser includes a pump laser to produce a pump beam at a pump wavelength and a nonlinear medium to convert said pump beam into a signal beam and an idler beam at two different wavelengths longer than said pump wavelength.

3. A spectrometer as in claim 1, further comprising a polarizer disposed to maintain a polarization of said sampling beam.

4. A spectrometer as in claim 1, further comprising a telescope disposed to reduce a cross sectional area of said sampling beam but making said sampling beam substantially collimated at said sample holder to keep its polarization substantially the same from one location in the cross section area to another.

5. A spectrometer as in claim 1, further comprising a sample chamber engaged to said sample holder to enclose the sample in a high temperature environment.

6. A spectrometer as in claim 1, further comprising a high-pressure diamond cell engaged to said sample holder to produce a high pressure on the sample.

7. A method for measuring spectroscopic properties of samples of minute quantities and microscopic dimensions, comprising:

generating a tunable monochromatic laser beam from optical parametric oscillation;

reducing the dimension of the laser beam to increase an intensity above a specified level;

dividing the laser beam into a reference beam and a sampling beam;

measuring and using the intensity of the reference beam to indicate an intensity of the sampling beam;

using a sampling aperture with a dimension less than 10 $\mu$m to limit spatial extent of the sampling beam;

exposing a sample to the sampling beam that transmits through the sampling aperture;

measuring the intensity of transmitted light from the sample; and tuning the wavelength of the laser beam to obtain the absorption spectrum of the sample.

8. A method as in claim 7, further comprising using a telescope to reduce the dimension of the laser beam and making laser beam substantially collimated at the sample to keep its polarization substantially the same from one location in the cross section area to another.

9. A method as in claim 7, further comprising:

placing a polarizer the in optical path of the laser beam; and keeping a polarization direction of the polarizer substantially aligned with a polarization of the laser beam to reduce fluctuation in the polarization of the sampling beam at the sample.

10. A method as in claim 7, further comprising using a sample chamber to enclose the sample in a high temperature environment.

11. A method as in claim 7, further comprising using a high-pressure diamond cell to produce a high pressure on the sample.

* * * * *